(12) United States Patent
Hausen

(10) Patent No.: US 8,523,939 B1
(45) Date of Patent: Sep. 3, 2013

(54) METHOD AND APPARATUS FOR HEART VALVE SURGERY

(75) Inventor: Bernard A. Hausen, Menlo Park, CA (US)

(73) Assignee: Cardica, Inc., Redwood City, CA (US)

( * ) Notice: Subject to any disclaimer, the term of this patent is extended or adjusted under 35 U.S.C. 154(b) by 1430 days.

(21) Appl. No.: 11/451,548

(22) Filed: Jun. 12, 2006

(51) Int. Cl.
*A61F 2/24* (2006.01)

(52) U.S. Cl.
USPC ........................................ 623/2.36; 623/2.38

(58) Field of Classification Search
USPC .............................................. 623/2.36, 2.16
See application file for complete search history.

(56) References Cited

U.S. PATENT DOCUMENTS

| | | | |
|---|---|---|---|
| 4,932,965 A | 6/1990 | Phillips | |
| 5,782,397 A * | 7/1998 | Koukline | 227/176.1 |
| 5,891,160 A | 4/1999 | Williamson, IV et al. | |
| 6,001,127 A | 12/1999 | Schoon et al. | |
| 6,096,074 A * | 8/2000 | Pedros | 623/2.1 |
| 6,409,758 B2 | 6/2002 | Stobie et al. | |
| 6,413,274 B1 | 7/2002 | Pedros | |
| 6,506,197 B1 | 1/2003 | Rollero et al. | |
| 6,695,866 B1 | 2/2004 | Kuehn et al. | |
| 6,726,716 B2 | 4/2004 | Marquez | |
| 6,730,118 B2 | 5/2004 | Spenser et al. | |
| 6,986,775 B2 | 1/2006 | Morales et al. | |
| 7,285,131 B1 * | 10/2007 | Bombard et al. | 623/1.36 |
| 2004/0030382 A1 * | 2/2004 | St. Goar et al. | 623/2.36 |
| 2004/0236419 A1 | 11/2004 | Milo | |
| 2004/0243230 A1 | 12/2004 | Navia et al. | |
| 2005/0065601 A1 | 3/2005 | Lee et al. | |
| 2005/0216079 A1 | 9/2005 | MaCoviak | |
| 2005/0251252 A1 | 11/2005 | Stobie | |
| 2005/0267572 A1 | 12/2005 | Schoon et al. | |
| 2006/0015179 A1 * | 1/2006 | Bulman-Fleming et al. | 623/2.36 |
| 2006/0025856 A1 * | 2/2006 | Ryan et al. | 623/2.11 |

* cited by examiner

*Primary Examiner* — David Isabella
*Assistant Examiner* — Joshua Levine
(74) *Attorney, Agent, or Firm* — Cardica, Inc.

(57) ABSTRACT

A method for heart valve surgery may include providing a cardiac valve ring and suture loops connected to the cardiac valve ring, accessing a valve annulus of the heart of the patient, stapling at least one of the sutures loop to the valve annulus, and parachuting the cardiac valve ring down the suture to the valve annulus after the stapling. The cardiac valve ring may be an annuloplasty ring, a replacement heart valve, or other medical device.

9 Claims, 4 Drawing Sheets

METHOD AND APPARATUS FOR HEART VALVE SURGERY

FIELD OF THE INVENTION

The invention relates to a method for performing heart valve surgery.

BACKGROUND

Annuloplasty is a procedure that treats or reconstructs a cardiac valve, usually the mitral valve. An annuloplasty ring is a device that are commonly used in that procedure. Referring to FIG. 1 an annuloplasty ring is sutured into place, in or near the tissue of a valve annulus 3 of the heart 1, and acts to reduce the circumference of the valve 5 adjacent to the valve annulus 3. The annuloplasty ring may be circular, shaped as a different closed shape, C-shaped, or shaped as another open shape, and may be rigid, semi-rigid or flexible. That ring is typically smaller in diameter than the valve being treated, in order to reduce its circumference. While the treatment of valve disease or incompetence with an annuloplasty ring is safe and effective, the installation of that annuloplasty ring is time-consuming due to the need to suture the annuloplasty ring in place, and as a result the patient must spend an appreciable amount of time connected to a heart-lung machine during the operation.

For patients with severe valve disease or incompetence, the affected valve 5 must be replaced in its entirety. The replacement valve is typically mechanical or porcine. During valve replacement surgery, the patient's heart valve is excised, and the replacement valve is sutured into place in its stead, in or near the tissue of the valve annulus 3. Valve replacement surgery is safe and effective, but as with annuloplasty, the installation of the replacement valve is time-consuming due to the need to suture the replacement valve in place.

BRIEF DESCRIPTION OF THE DRAWINGS

The use of the same reference symbols in different figures indicates similar or identical items.

DETAILED DESCRIPTION

Figure 1:
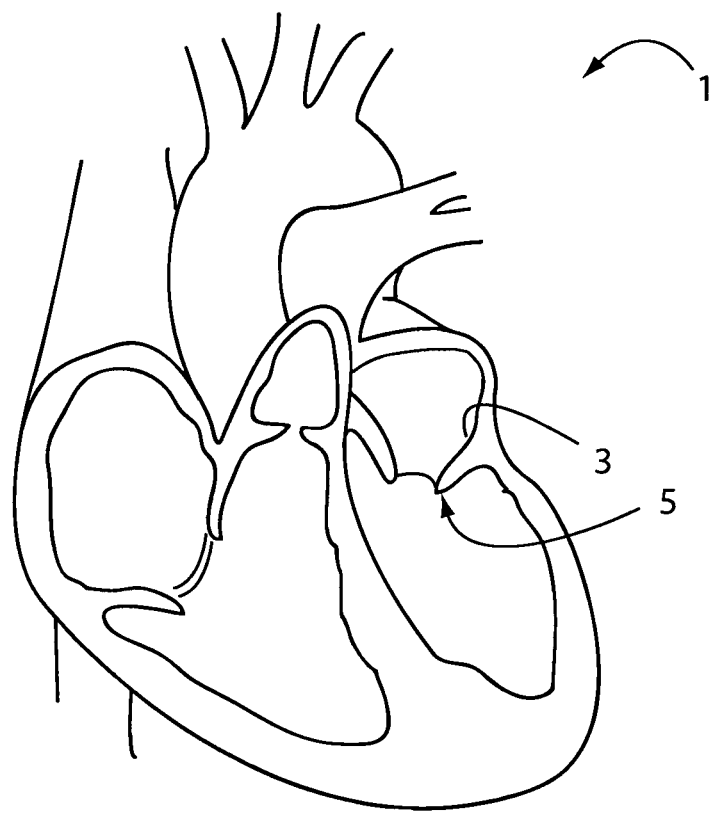
FIG. 1 is a cross-section view of a human heart.

Referring to FIG. 1, a cardiac valve ring 2 is shown. As used in this document, the term "cardiac valve ring" refers to all and/or part of a device surgically implanted in a patient for treatment of a heart valve disease or incompetence. The scope of the term "cardiac valve ring" covers annuloplasty rings of any shape, material or configuration, as well as replacement heart valves, whether mechanical or porcine.

Two or more apertures 4 are provided through the cardiac valve ring 2. Advantageously, the apertures 4 are paired in groups of two, with the pairs spaced substantially evenly about the cardiac valve ring 2. However, the apertures 4 need not be paired. Further, the apertures 4 need not be spaced evenly about the cardiac valve ring 2. The apertures 4 are advantageously oriented substantially parallel to the longitudinal centerline of the cardiac valve ring 2 or the axis of radial symmetry of the cardiac valve ring 2, which are coincident when the cardiac valve ring 2 is substantially annular. However, the apertures 4 may be oriented differently, if desired.

At least one strand of suture 6 is connected to the cardiac valve ring 2. The suture 6 may be composed of any suitable material, such as but not limited to polypropylene or wire. As one example, each strand of suture 6 passes through the cardiac valve ring 2 twice, such that it forms a U-shaped configuration. Both ends of that strand of suture 6 are positioned on the proximal side of the cardiac valve ring 2. Moving distally from one end of that strand of suture 6, the suture 6 extends through one aperture 4 on the cardiac valve ring 2, extends a distance distal to the cardiac valve ring 2, then curves back in the proximal direction and through a different aperture 4, ending at a location proximal to the cardiac valve ring 2. As a result, the portion of the strand of suture 6 distal to the cardiac valve ring 2, and the portion of the cardiac valve ring 2 between the two apertures 4 through which that strand of suture 6 passes, together form a closed perimeter. The portion of the strand of suture 6 distal to the cardiac valve ring 2 may be referred to as a suture loop 8. The suture loop 8 may be U-shaped. That is, the suture loop 8 may be open at one end, where that end is connected to the cardiac valve ring 2. The two apertures 4 through which a particular strand of suture 6 passes are advantageously each part of a set of paired apertures. Advantageously, a number of separate and independent sutures 6 are connected to the cardiac valve ring 2 in this manner, or in any other suitable manner.

Figure 2:
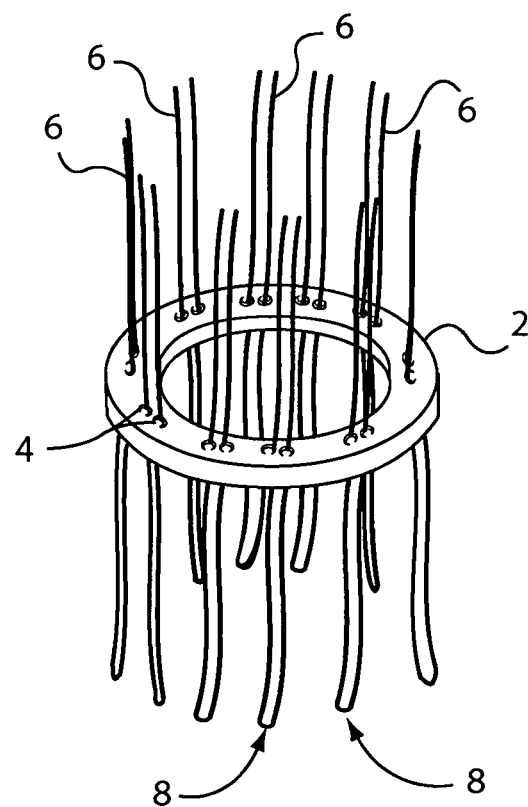
FIG. 2 is a perspective view of a cardiac valve ring having a plurality of suture loops.

As another example, referring to FIG. 2, at least one individual strand of suture 6 passes through the cardiac valve ring 2 once. The distal end of each strand of suture 6 is pre-tied or manufactured in any suitable manner to have at least one suture loop 8 therein. This configuration of the suture loop 8 may be characterized as lasso-shaped. The suture loop 8 may be collapsible, such that the suture loop 8 decreases in size as tension is applied to the suture 6 in the proximal direction. Alternately, the suture loop 8 may have a constant size that does not substantially change as tension is applied to the suture 6 in the proximal direction. As another example, at least one suture loop 8 is J-shaped, where one end of the suture 6 is fixed to the cardiac valve ring 2. That suture 6 extends a distance distal to the cardiac valve ring 2, then curves back in the proximal direction and through an aperture 4, ending at a location proximal to the cardiac valve ring 2.

Figure 3:
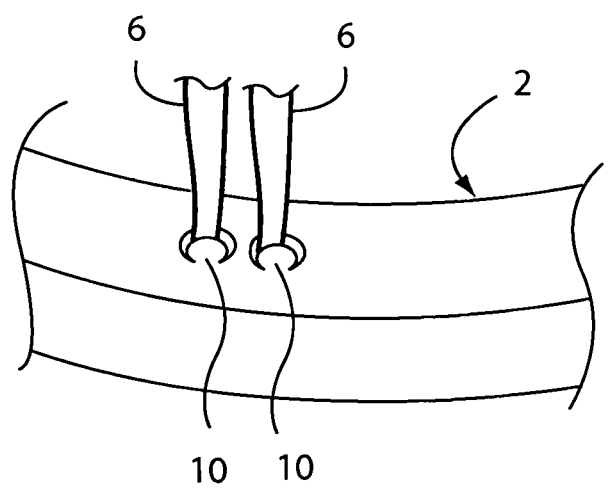
FIG. 3 is a detail perspective view of the cardiac valve ring of FIG. 2.

The apertures 4 may be of any suitable shape and cross-section. As one example, at least one aperture 4 is substantially cylindrical. As another example, at least one aperture 4 is substantially rectangular or square in cross-section. Referring to FIG. 3, optionally at least one tab 10 is associated with each aperture 4. Advantageously, one tab 10 is associated with each aperture 4, and is positioned at or in proximity to the end of each aperture 4. Each tab 10 may be formed integrally with the cardiac valve ring 2, or may be attached to the cardiac valve ring 2 in any suitable manner, such as by welding. Each tab 10 is sized to be slightly smaller than the cross-section of the aperture 4 at a location adjacent to that tab 10. Advantageously, the space between the tab 10 and the perimeter of the aperture 4 adjacent to the tab 10 is less than the diameter of the suture 6 passing through that aperture 4. Each tab 10 is deflectable to allow motion of the suture 6 through the aperture 4 when tension is applied to that suture 6. Further, each tab 10 is configured to flex back toward its original position after tension is removed from the suture 6, in order to press the suture 6 against the aperture 4 and thereby hold the suture 6 substantially in place. Advantageously, at least part of each tab 10 is spaced from the corresponding aperture 4 a distance less than the diameter of the suture 6. The combination of each tab 10 and the corresponding aperture 4 may be referred to as a unidirectional suture holding features, and allows the suture 6 to be pulled in one direction and then remain in place after tension on the suture is released. Alternately, at least one unidirectional suture holding features may be configured in any other suitable manner.

A stapler is utilized in conjunction with the cardiac valve ring 2. The stapler may be of any suitable configuration, and is not limited to any particular stapler or type of staple. As one example, the stapler and the staple may be as set forth in U.S. patent application Ser. No. 11/093,003, filed on Mar. 28, 2005, which is hereby incorporated by reference in its entirety. As another example, the stapler and the staple may be as set forth in U.S. patent application Ser. No. 11/158,414, filed on Jun. 22, 2005, which is hereby incorporated by reference in its entirety. The staples described in the above-referenced patent applications first splay outward, then close, during deployment. Alternately, a clip applier may be used instead of a stapler.

Operation

Referring also to FIG. 1, the surgeon gains access to the heart valve 5 to be reinforced or replaced in any suitable manner. The surgical approach to that heart valve 5 is standard in the art. Referring to FIG. 1, the cardiac valve ring 2 is moved relative to the valve annulus 3 such that at least one suture loop 8 is in proximity to the valve annulus 3. At this point, the cardiac valve ring 2 itself is spaced apart from the valve annulus 3, and may be held by the surgeon, an assistant, a mechanical fixture such as a clamp, or by any other suitable structure, mechanism or method.

Figure 4:
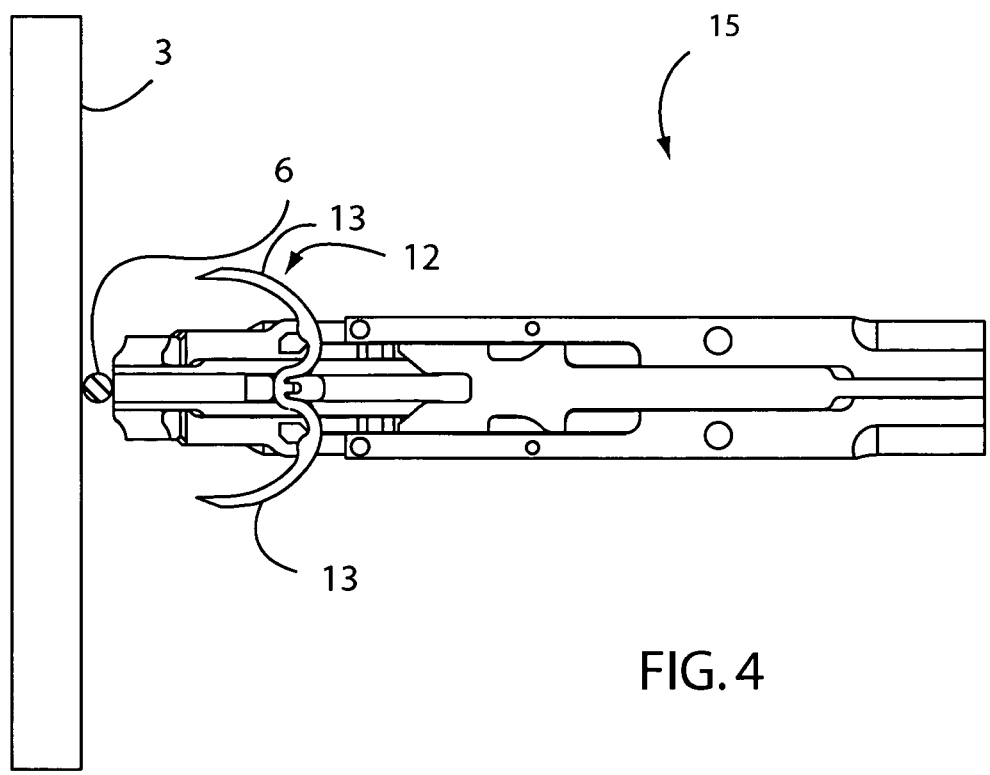
FIG. 4 is a side cross-section view of a stapler approaching a valve annulus of the heart.
Figure 5:
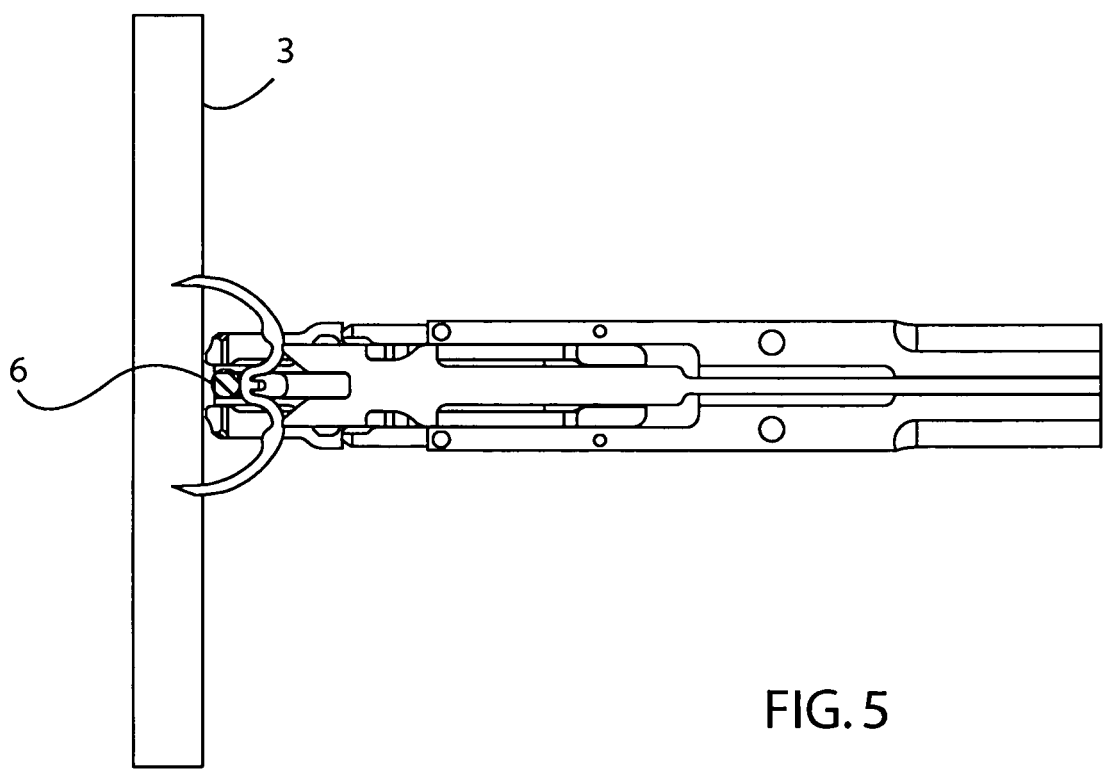
FIG. 5 is a side cross-section view of the stapler of FIG. 4, where a staple held by that stapler is straddling a suture loop of the cardiac valve ring of FIG. 2.
Figure 6:
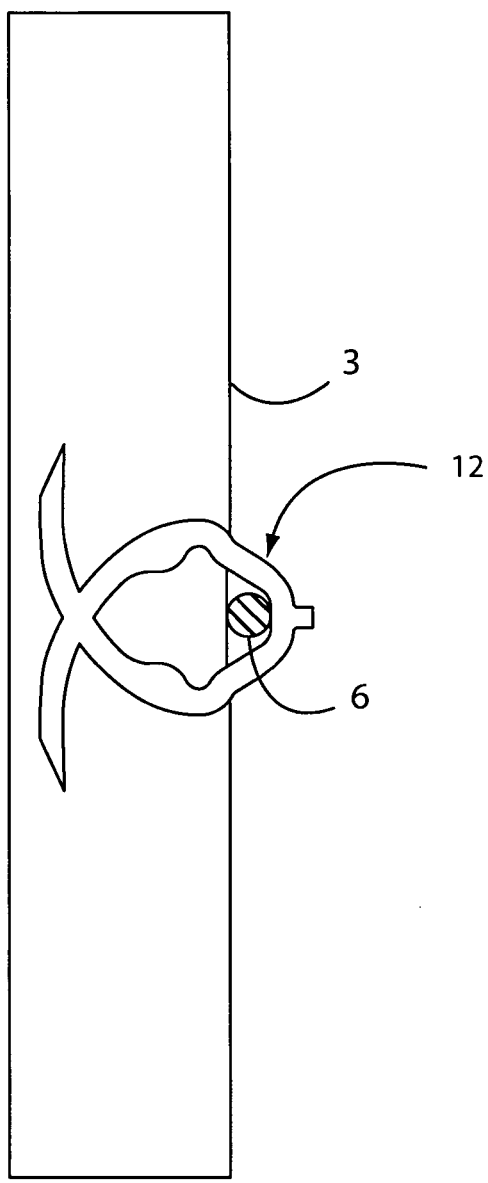
FIG. 6 is a side cross-section view of the staple of FIGS. 4-5 in a deformed position, attaching the suture loop to the valve annulus.

Next, the surgeon staples each suture loop 8 to the valve annulus 3. Referring to FIGS. 4-6, the stapler 15 and staples 12 that are utilized may be substantially as disclosed in U.S. patent application Ser. Nos. 11/093,003 or 11/158,414, or may be in any other configuration. Stapling may be performed in any suitable manner. Initially, referring to FIG. 4, the stapler 15 is moved into proximity to a suture loop 8 and to the valve annulus 3. The stapler 15 carries a staple 12 that may be already in a splayed position as shown in FIG. 4, or that may be moved or deformed to a splayed position after the stapler 15 is moved into proximity to a suture loop 8.

Next, referring also to FIG. 5, the stapler 15 is advanced relative to the valve annulus 3 to a position where one leg 13 of the staple 12 is positioned on one side of the suture 6 and one leg 13 of the staple 12 is positioned on the other side of the suture 6, such that the staple 12 straddles the suture 6 of the suture loop. The stapler 15 continues to be advanced, such that at least one leg 13 of the staple 12 contacts or penetrates the tissue of the valve annulus 3. The stapler 15 is then actuated to close the staple 12, thereby trapping the suture 6 of the suture loop 8 between the tissue of the valve annulus 3 and the staple 12, as shown in FIG. 6. In this way, the suture loop 8 is attached to the valve annulus 3.

The stapler is then moved to another suture loop 8, which it attaches to the valve annulus 3 in substantially the same manner as described above. That is, the suture loops 8 are successively attached to the valve annulus 3. Alternately, a different stapler may be used. Alternately, more than one or all of the staples 12 may be deployed at the same time, where each staple 12 captures a different suture loop 8. The stapler 15 may carry a plurality of staples 12, and/or may be reloaded at least once during the process of attaching the suture loops 8 to the valve annulus 3.

After the suture loops 8 have been connected to the valve annulus 3, the cardiac valve ring 2 is parachuted down the sutures 6 into position in the valve annulus 3. Parachuting refers to the sliding of the cardiac valve ring 2 down the sutures 6, and is a term that is standard in the art. Each tab 10 is deflected away from the corresponding aperture 4 as the sutures 6 are held in tension and the cardiac valve ring 2 is pushed along those sutures 6, such that the deflection of the tabs 10 allows the cardiac valve ring 2 to move relative to the sutures 6.

After the cardiac valve ring 2 reaches and is seated properly in the valve annulus 3, the sutures 6 may be released. At this point, each tab 10 moves back toward the corresponding aperture 4, pressing the suture 6 that extends through that aperture 4 between the tab 10 and the aperture 4 and holding that suture 6 in place. By holding the sutures in place, the tabs 10 in turn hold the cardiac valve ring 2 in place. Optionally, to provide additional security, the proximal ends of the suture 6 of at least one suture loop 8 may be tied together. Alternately, a proximal end of at least one suture 6 may be tied to a proximal end of at least one other suture 6, to provide additional security. One or both free ends of least one suture 6 may then be severed in proximity to the cardiac valve ring 2 or at any other suitable location, such that a short portion of suture 6 remains for each corresponding tab 10 and aperture 4 to engage. The valve reinforcement or replacement procedure is now complete.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Further, the invention is not limited to the performance of heart valve surgery. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical method performed on a valve annulus of the heart of a patient, the heart including a natural heart valve composed of native tissue of the patient, where the valve annulus is located adjacent to the natural heart valve, comprising:

providing an annuloplasty ring and a plurality of suture loops connected to said annuloplasty ring, said suture loops formed from lengths of suture wherein at least one of said suture loop is U-shaped;

accessing the valve annulus of the heart of the patient, adjacent to the natural heart valve;

stapling at least one said suture loop to the valve annulus with at least one staple; and moving said annuloplasty ring down said suture to the valve annulus to a position adjacent to the natural heart valve, after said stapling.

2. The method of claim 1, wherein said stapling includes straddling said suture of said suture loop with said staple, and closing said staple after said straddling.

3. The method of claim 2, wherein said stapling includes penetrating the valve annulus with said staple before said closing.

4. The method of claim 1, further comprising holding said annuloplasty ring in a fixed position relative to said valve annulus after said moving.

5. The method of claim 1, wherein said moving is along said suture in only a single direction.

6. The method of claim 1, further comprising severing at least one said suture in proximity to said cardiac valve ring after said moving.

7. The method of claim 1, further comprising splaying at least one said staple before said stapling.

8. The method of claim 1, wherein said stapling comprises successively stapling individual suture loops.

9. The method of claim 1, wherein each length of suture has a first end and a second end, further comprising tying said first end of at least one said suture to said second end.

\* \* \* \* \*